United States Patent
Jin et al.

[11] Patent Number: 6,166,243
[45] Date of Patent: Dec. 26, 2000

[54] PROCESS FOR THE PREPARATION OF INSECTICIDAL PHENYLHYDRAZINE DERIVATIVES

[75] Inventors: Haihong Jin, Glastonbury; Joseph A. Feiccabrino, Naugatuck, both of Conn.

[73] Assignee: CK Witco Corporation, Middlebury, Conn.

[21] Appl. No.: 09/430,961

[22] Filed: Nov. 1, 1999

[51] Int. Cl.$^7$ ..................... C07C 269/04; C07C 231/02
[52] U.S. Cl. ................... 560/27; 562/39; 564/34; 564/101; 564/137; 564/141; 564/143; 564/144; 564/310; 564/314
[58] Field of Search ................ 560/27; 562/39; 564/37, 137, 141, 143, 144, 101, 310, 314

[56] References Cited

U.S. PATENT DOCUMENTS 2,547,724  4/1951  Sundholm ......................... 167/33

(List continued on next page.)

FOREIGN PATENT DOCUMENTS 0067471  5/1982  European Pat. Off. .

(List continued on next page.)

OTHER PUBLICATIONS

Chemical Abstracts 105(17):152686c (1986).

(List continued on next page.)

*Primary Examiner*—Peter O'Sullivan
*Attorney, Agent, or Firm*—Raymond D. Thompson; Paul Grandinetti

[57] ABSTRACT

Disclosed herein is a method for making compounds having the structural formulae (I) or (II):

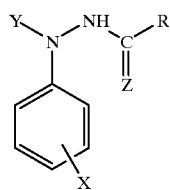

I

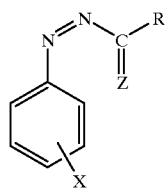

II wherein: X is a) phenyl; lower phenylalkoxy; phenoxy; or benzyl; or b) one substituent from group a) and one or more substituents selected from $C_1$–$C_4$ alkoxy; hydroxyl; halogen; lower alkyl; and lower alkylthio; or c) along with the phenyl to which it is attached, forms a multiple fused ring heterocycle such as dibenzofuranyl; Y is H, $C_1$–$C_4$ alkanoyl, $C_1$–$C_4$ haloalkanoyl dialkoxyphosphoryl, alkylaminocarbonyl, haloalkylsulfonyl, or $C_1$–$C_4$ alkoxy carbonyl; and R is H, $C_1$–$C_6$ alkyl, $C_1$–$C_6$ alkoxy, $C_3$–$C_6$ cycloalkoxy, haloalkyl, alkoxyalkyl, arylalkoxy, alkenyl, alkylthio, alkoxycarbonyl, alkylamino, heteroaryl, arylalkyl, haloalkoxy, aryloxy, or $C_3$–$C_6$ cycloalkyl; and Z is O or S, wherein the process comprises the steps of:

A) selecting as a starting material a compound of the structural formula

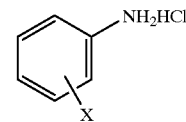

III

B) reacting compound III with sodium nitrite in the presence of HCl to form the diazonium salt IV

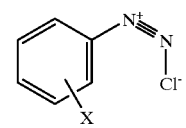

IV

C) adding compound IV to freshly prepared alkali metal sulfite prepared by purging sulfur dioxide into an alkali metal hydroxide until the pH is between 7.3 and 7.5, thereby forming compound V

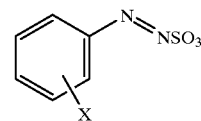

V

D) reducing compound V with an alkali metal dithionite to form compound VI

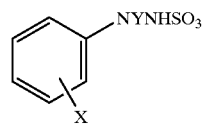

VI

E) hydrolyzing compound VI under aid conditions to form compound VII

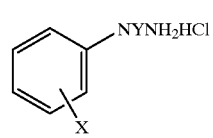

VII and

F) acylating compound VII to form compound I.

8 Claims, No Drawings

U.S. PATENT DOCUMENTS

| | | | |
|---|---|---|---|
| 4,725,302 | 2/1988 | Ehrenfreund | 71/88 |
| 5,367,093 | 11/1994 | Dekeyser et al. | 560/27 |
| 5,438,123 | 8/1995 | Dekeyser et al. | 534/885 |

FOREIGN PATENT DOCUMENTS

| | | |
|---|---|---|
| 93/10083 | 11/1992 | WIPO . |
| 97/40692 | 4/1997 | WIPO . |
| 98/17637 | 10/1997 | WIPO . |

OTHER PUBLICATIONS

Chemical Abstracts 108(19):163280d (1988).
DerWent Abstract 88–312695/44 (1988).
Chemical Abstract 126:86070 (1996).

PROCESS FOR THE PREPARATION OF INSECTICIDAL PHENYLHYDRAZINE DERIVATIVES

BACKGROUND OF THE INVENTION

1. Field of the Invention

The present invention is directed to novel process for the preparation of phenylhydrazine derivatives that exhibit activity as insecticides, acaricides, and nematicides. The present invention is also directed to processes for the preparation of intermediates useful in the manufacture of such phenylhydrazine derivatives.

2. Description of Related Art

Destruction by insects, acarids, and nematodes presents a serious problem to agriculture. A wide variety of field crops are in need of protection from nematodes, acarids, and insects including such valuable crops as soybeans, corn, peanuts, cotton, alfalfa, rice, and tobacco. In addition, vegetables, such as, tomatoes, potatoes, sugar beets, carrots, peas, and the like, as well as fruits, nuts, ornamentals, and seed bed crops, such as, apples, peaches, almonds, citrus fruit, and grapes may also require protection from the ravages of such pests.

Consequently, the development of new, more effective, pesticides, including insecticides, acaricides, and nematicides, and processes for the preparation thereof represent an ongoing scientific activity.

Chemical Abstracts 105(17):152686c refers to various phenylhydrazines said to have activity against insects and mites.

Chemical Abstracts 108(19):163280d refers to alkyl phenylhydrazinecarboxylates said to be usefull as acaricides.

DerWent abstract 88-312695/44 refers to arylhydrazides of trifluoroacetic acid said to have fungicidal, bacteriocidal, acaricidal, and antiseptic activity.

WO 98/17637 is directed to compounds having the structural formula

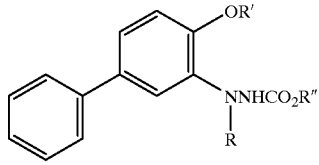

wherein:
R is $C_1$–$C_6$ hydroxyalkyl, $C_1$–$C_6$ haloalkyl, $C_1$–$C_6$ alkyl, $C_7$–$C_9$ aralkyl, or nitroso; R' is $C_1$–$C_4$ alkyl; and R" is $C_1$–$C_4$ alkyl. These compounds exhibit insecticidal and miticidal activity.

European Patent 0 067 471 refers to 7-substituted 2,3-dihydrobenzofurans said to be useful as pesticides or chemical intermediates.

U.S. Pat. No. 4,725,302 refers to substituted phenylhydrazines and phenyloxadiazolinones said to be useful as pesticides.

U.S. Pat. Nos. 5,367,093 and 5,438,123 and WO 93/10083 relate to compounds having the structural formulae (I) or (II) described below. These compounds are effective for controlling mites, nematodes, rice planthopper, tobacco budworm, and southern corn rootworm. Methods for making these compounds are also set forth.

WO 97/40692 discloses a composition for insects and representatives of the order Acarina, which comprises a combination of variable amounts of one or more compounds of the formula

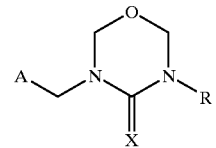

in which A is an unsubstituted or, depending on the possibility of substitution on the ring system, mono- to tetrasubstituted, aromatic or non-aromatic monocyclic or bicyclic heterocyclic radical, in which the substituents of A can be chosen from the group consisting of to $C_1$–$C_3$ alkyl, $C_1$–$C_3$ alkoxy, halogen, halo-, cyclopropyl, halocyclopropyl, $C_2$–$C_3$ alkenyl, $C_2$–$C_3$ alkynyl, halo-$C_1$–$C_3$ alkoxy, $C_1$–$C_3$ alkylthio, halo $C_1$–$C_3$ alkylthio, allyloxy, propargyloxy, allylthio, propargylthio, haloallyloxy, haloallylthio, cyano, and nitro; R is hydrogen, $C_1$–$C_6$ alkyl phenyl-$C_1$–$C_4$ alkyl, $C_3$–$C_6$ cycloalkyl, $C_2$–$C_6$ alkenyl or $C_2$–$C_6$ alkynyl; and X is N-$NO_2$ or N-CN, in the free form or in the salt form, if appropriate tautomers, in the free form or salt form, and one or more compounds mentioned in the specification and at least one auxiliary. A method of controlling pests, a process for the preparation of the composition, its use and plant propagation material treated with it, and use of the compound of the above formula for the preparation of the composition are also described.

Dekeyser et al., Brighton Crop Prot. Conf.-Pests Dis. Vol.2:487–492 (1996) discloses N'-(4-methoxybiphenyl-3-yl)hydrazinecarboxylic acid, iso-PR ester (D2341) as a novel acaricide for mite control in agricultural and ornamental crops. The compound has a good toxicological and environmental profile. D2341 shows no cross-resistance with currently available acaricides and provides excellent control at low rates against all stages of tetranychid mites and motile forms of Panonychus species. Proposed field rates are 0.15–0.60 kg/ha for the control of Panonychus urticae. D2341 has outstandingknockdown and residual activity for control of many phytophagous mites. It shows minimal impact on beneficial insects and mites. It is therefore recommended in integrated pest management programs. In trials on apples and citrus, D2341 has shown no crop injury at rates well in excess of proposed field rates.

The disclosures of the foregoing are incorporated herein by reference in their entirety.

SUMMARY OF THE INVENTION

The present invention relates to a method for making compounds having the structural formulae (I) or (II):

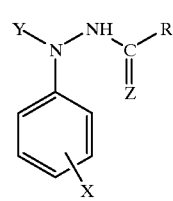

-continued

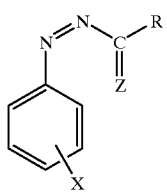
II wherein:

X is a) phenyl; lower phenylalkoxy; phenoxy; or benzyl; or b) one substituent from group a) and one or more substituents selected from $C_1$–$C_4$ alkoxy; hydroxyl; halogen; lower alkyl; and lower alkylthio; or c) along with the phenyl to which it is attached, forms a multiple fused ring heterocycle such as dibenzofuranyl; Y is H, $C_1$–$C_4$ alkanoyl, $C_1$–$C_4$ haloalkanoyl, dialkoxyphosphoryl, alkylaminocarbonyl, haloalkylsulfonyl, or $C_1$–$C_4$ alkoxy carbonyl; and R is H, $C_1$–$C_6$ alkyl, $C_1$–$C_6$ alkoxy, $C_3$–$C_6$ cycloalkoxy, haloalkyl, alkoxyalkyl, arylalkoxy, alkenyl, alkylthio, alkoxycarbonyl, alkylamino, heteroaryl, arylalkyl, haloalkoxy, aryloxy, or $C_3$–$C_6$ cycloalkyl; and Z is O or S, wherein the process comprises the steps of:

A) selecting as a starting material a compound of the structural formula

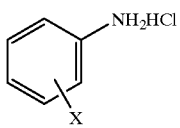
III

B) reacting compound III with sodium nitrite in the presence of HCl to form the diazonium salt IV

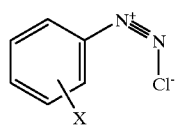
IV

C) adding compound IV to freshly prepared alkali metal sulfite prepared by purging sulfur dioxide into an alkali metal hydroxide until the pH is between 7.3 and 7.5, thereby forming compound V

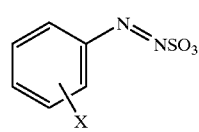
V

D) reducing compound V with an alkali metal dithionite to form compound VI

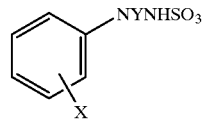
VI

E) hydrolyzing compound VI under acid conditions to form compound VII

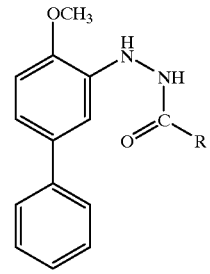
VII and

F) acylating compound VII to form compound I.

Further, when X includes a substituent having a phenyl ring (i.e., is phenyl, phenylalkoxy, phenoxy or benzyl), the phenyl ring is optionally substituted with one or more of halogen, nitro, lower alkyl, lower alkoxy, lower haloalkyl, or dialkylamino.

In a particularly preferred embodiment, the present invention is directed to a method for making compounds having the structural formula I:

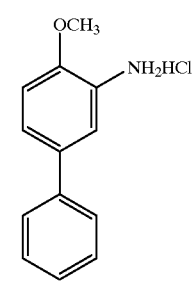
I wherein R is $C_1$–$C_6$ alkoxy, comprising the steps of:

A) selecting as a starting material a compound of the structural formula

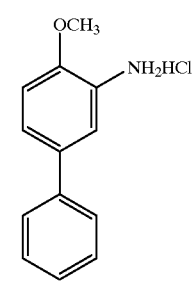
III

B) reacting compound III with sodium nitrite in the presence of HCl to form the diazonium salt IV IV
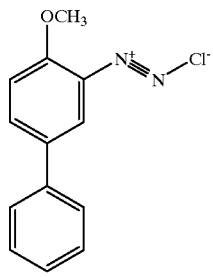

C) adding compound IV to freshly prepared alkali metal sulfite prepared by purging sulfur dioxide into an alkali metal hydroxide until the pH is between 7.3 and 7.5, thereby forming compound V V
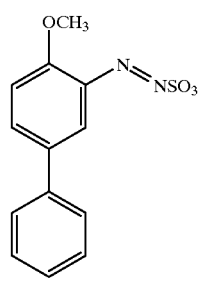

D) reducing compound V with an alkali metal dithionite to form compound VI

VI
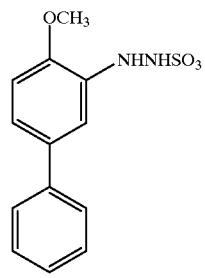

E) hydrolyzing compound VI under acid conditions to form compound VII

VII
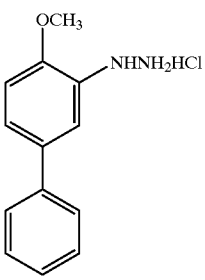

and

F) acylating compound VII to form compound I.

DESCRIPTION OF THE PREFERRED EMBODIMENTS

The compounds prepared by the process of the present invention have the structure (I) or (II) defined above. Preferred compounds are those in which Y is hydrogen, X is phenyl and $C_1$–$C_4$ alkoxy, Z is oxygen, and R is $C_1$–$C_6$ alkyl. The most preferred compound is 2-(4-methoxy[1,1'-biphenyl]-3-yl)hydrazinecarboxylic acid, 1-methylethyl ester (also known as isopropyl 3-(4-methoxy-3-biphenylyl) carbazate or Bifenazate).

The compounds having structure (I) are prepared by a series of reactions represented by the following:

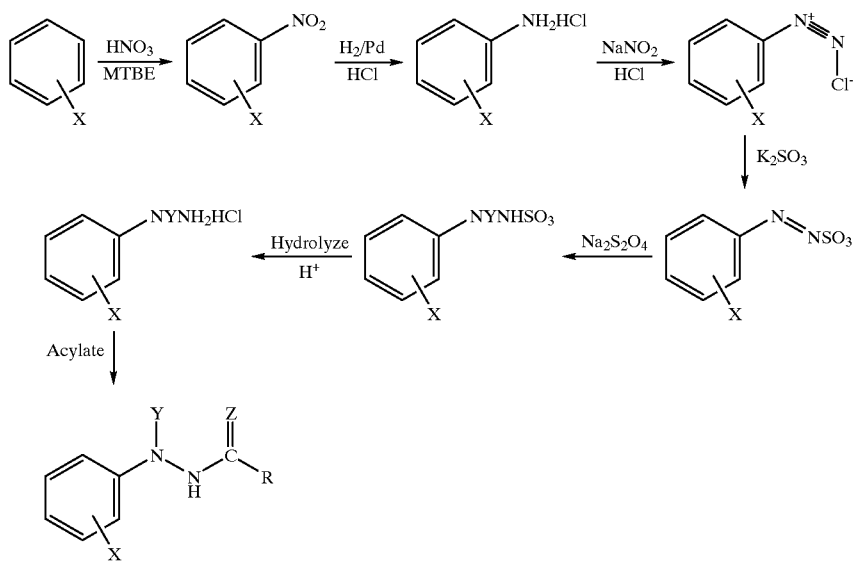

where X, Y, Z, and R are as described above.

The final product of this reaction may be further acylated, or converted by oxidation with an oxidizing agent such as Pd/air to form compounds having structure (II).

3-Amino-4-methoxybiphenyl hydrochloride is a crucial intermediate in the synthesis of Bifenazate. It is commercially available, but is too expensive to permit use of the commercial material on a large scale. It is thus an object of the present invention to provide an inexpensive route for the manufacture of 3-amino-4-methoxybiphenyl hydrochloride. This object has been accomplished by starting with 4-hydroxybiphenyl and nitrating it to form 3-nitro-4-hydroxybiphenyl. For the nitration, a novel method, which was carried out in a suitable organic solvent, was developed. The nitration was realized by dissolving the 4-hydroxybiphenyl in an organic solvent, such as, methyl t-butyl ether (BE), and nitrating it with commercially available 69%–71% nitric acid.

Several organic solvents, in addition to MBTE have been tried, including ethylene glycol dimethyl ether (Glyme), 2-methoxyethyl ether (Diglyme), acetone, acetic acid, and trifluoroacetic acid, and it has been found that the choice of organic solvent has a great impact on the nitration Yield and purity of the product. See Table I.

TABLE I

Nitration of 4-Hydroxybiphenyl

| Solvent | Nitration (yield %) |
| --- | --- |
| MTBE | 95–99 |
| Glyme | 95–98 |
| Diglyme | 90–95 |
| Acetonitrile | 90–95 |
| Acetic Acid | 90–95 |
| Acetone | No reaction |
| Trifluoroacetic acid | No reaction |

The traditional nitration method using a mixture of sulfuric acid and nitric acid was also used with 4-hydroxybiphenyl, but it was found that a large quantity of by-products was formed.

After the 3-nitro-4-hydroxybiphenyl is formed as described above, it is then reacted with dimethylsulfate to form 3-nitro-4-methoxybiphenyl, which is then reduced to form 3-amino-4-methoxybiphenyl. The 3-amino-4-methoxybiphenyl is precipitated by the addition of hydrochloric acid solution, forming the desired 3-amino-4-methoxybiphenyl hydrochloride.

Additionally, unlike other methods known in the art, which involve the use of heavy metal inorganic salts, such as, lanthanum nitrate hexahydrate, copper(II) nitrate, and ferric nitrate nonahydrate, the improved method of the present invention not only produces 3-amino-4-methoxybiphenyl hydrochloride in high yield, but also produces less waste.

The foregoing may be represented by the following:

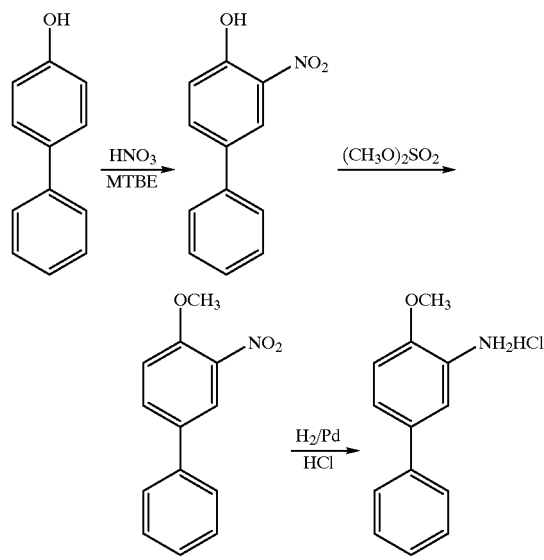

The 3-amino-4-methoxybiphenyl hydrochloride prepared as above can then be converted to the 4-methoxy-3-biphenyldiazonium salt by reaction with sodium nitrite by means of the well-known diazonium reaction. In the meantime, fresh potassium sulfite solution is prepared by purging sulfur dioxide into potassium hydroxide until the pH is between 7.3 and 7.5. The 4-methoxy-3-biphenyldiazonium salt is then added to the freshly prepared potassium sulfite solution at 0° C. to form 4-methoxy-3-biphenyldiazo sulfonate.

The discovery of the use of freshly prepared alkali metal sulfite as a reducing agent is of great importance in the preparation of Bifenazate. Only the freshly prepared sulfite solution, prepared from alkali metal hydroxide and sulfur dioxide, was found to have the ability to reduce the diazonium salt to the diazosulfonate compound. Commercially available sodium sulfite and potassium sulfite were tried, but none of the desired product was formed, only a black tar. Sodium sulfite made by neutralizing sulfurous acid with two molar equivalents of sodium hydroxide was also tested in the reaction, but only a low yield was achieved. See Table II.

TABLE II

Yield of 4-Methoxy-3-Biphenylhydrazine Hydrochloride using Different Sulfite Solutions

| Sulfite Solution | Yield |
| --- | --- |
| $Na_2SO_3$ (Commercial) | Black tar |
| $Na_2SO_3$ (NaOH + $H_2SO_3$) | 40–50% |
| $Na_2SO_3$ (NaOH + $SO_2$) | 60–65% |
| $K_2SO_3$ (KOH + $SO_2$) | 88–97% |

The 4-methoxy-3-biphenyldiazo sulfonate formed above was then further reduced to 4-methoxy-3-biphenylhydrazine sulfonate with sodium dithionite, which was followed by hydrolysis under acid conditions to form 4-methoxy-3-biphenylhydrazine hydrochloride. This product can then be reacted with isopropylchloroformate to form Bifenazate, i.e.,

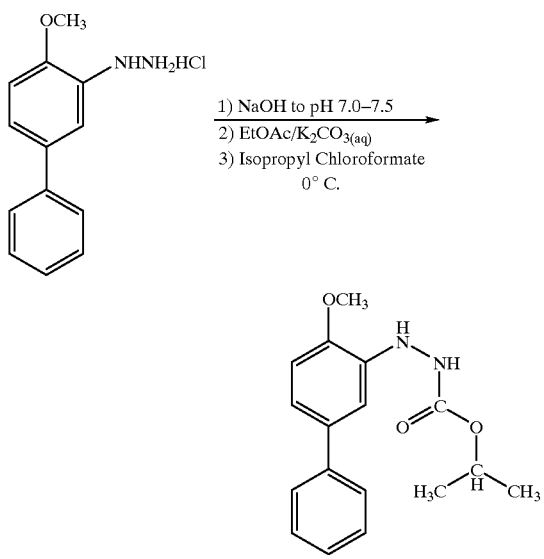

The foregoing reactions may be summarized by the following:

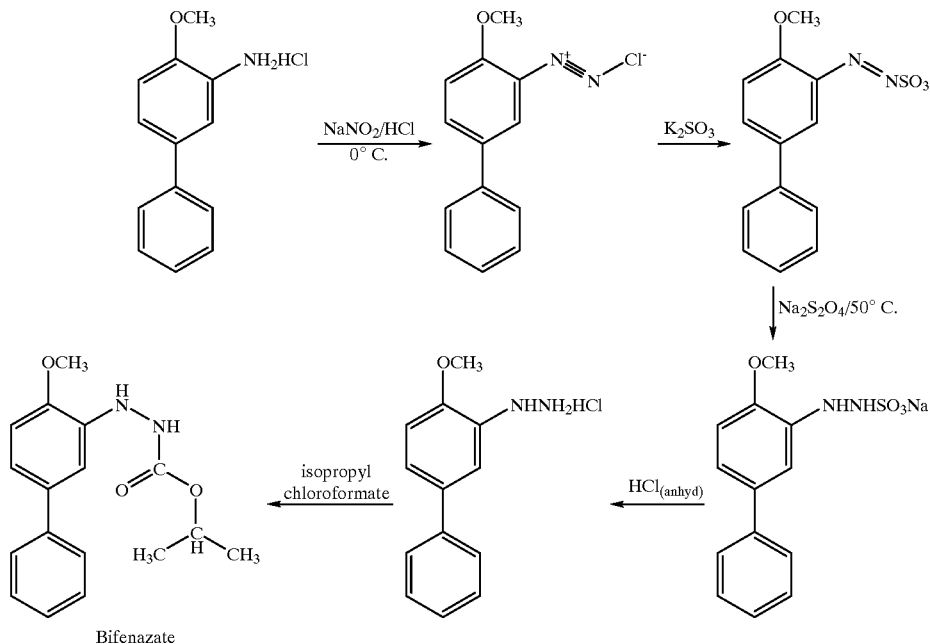

prepared by the process of the present invention may be applied as dusts when admixed with or adsorbed onto powdered solid carriers, such as mineral silicates, e.g., mica, talc, pyrophyllite and clays, together with a surface-active dispersing agent so that a wettable powder is obtained that then is applicable directly to the loci to be treated.

Alternatively, the powdered solid carrier containing the compound admixed therewith may be dispersed in water to form a suspension for application in such form. Granular formulations of the compounds, suitable for application by broadcasting, side dressing, soil incorporation or seed treatment, are suitably prepared using a granular or pellitized form of carrier such as granular clays, vermiculite, charcoal, or corn cobs.

Alternatively, the pesticidal compounds may be applied in liquids or sprays when utilized in a liquid carrier, such as in a solution comprising a compatible solvent such as acetone, benzene, toluene, or kerosene, or as dispersed in a suitable non-solvent medium, for example, water.

Another method of application to loci to be treated is aerosol treatment, for which the compound may be dissolved in an aerosol carrier that is a liquid under pressure but which is a gas at ordinary temperature (e.g., 20° C.) and atmospheric pressure. Aerosol formulations may also be prepared by first dissolving the compound in a less volatile solvent and then admixing the resulting solution with a highly volatile liquid aerosol carrier.

Compositions can be prepared from the compounds prepared by the process of this invention by mixing a compound having a structure of formula (I) or (II) above with a suitable carrier. Such suitable carriers may be solid or liquid in nature. Suitable liquid carriers may be comprised of water, alcohols, ketones, phenols, toluene, and xylenes. In such formulations, additives conventionally employed in the art may be utilized such as, for example, one or more surface active agents and/or inert diluents, to facilitate handling an application of the resulting pesticide composition. The pesticidal compositions may alternatively comprise solid carriers taking the form of dusts, granules, wettable powders, pastes, aerosols, emulsions, emulsifiable concentrates, and water-soluble solids. For example, the pesticidal compounds For pesticidal treatment of plants (such term including plant parts), the compounds prepared employing the process of the present invention preferably are applied in aqueous emulsions containing a surface-active dispersing agent, which may be non-ionic, cationic, or anionic. Suitable surface-active agents include those known in the art, such as those disclosed in U.S. Pat. No. 2,547,724 (columns 3 and 4). The compounds may be mixed with such surface-active dispersing agents, with or without an organic solvent, as concentrates for the subsequent addition of water to yield aqueous suspensions of the compounds at desired concentration levels. In addition, the compounds may be employed with carriers which themselves are pesticidally active, such as, insecticides, acaricides, fungicides, or bactericides.

It will be understood that the amount of the pesticidally active compound in a given formulation will depend upon the specific pest to be combatted, as well as upon the specific chemical composition and formulation of the compound being employed, the method of applying the compound/ formulation and the locus of treatment so that the pesticidally effective amount of the compound may vary widely. Generally, however, concentrations of the compound as the active ingredient in pesticidally effective formulations may range from about 0.1 to about 95 percent by weight. Spray dilutions may be as low as a few parts per million, while at the opposite extreme, full strength concentrates of the compound may be usefully applied by ultra low volume techniques. Concentration per unit area, where plants constitute the loci of treatment, may range between about 0.01 and about 50 pounds per acre, with concentrations of between about 0.1 and about 10 pounds per acre preferably being employed for crops such as corn, tobacco, rice, and the like.

To combat pests, sprays of the compounds may be applied to the pests directly and/or to plants upon which they feed or nest. The pesticidally active formulations may also be applied to the soil or other medium in which the pests are present. Harmful insects, nematodes, and acarids attack a wide variety of plants, including both ornamental and agricultural plants and inflict damage by consuming roots and/or foliage, withdrawing vital juices from the plants, secreting toxins, and often by transmitting diseases. The compounds prepared by the process of the present invention may be advantageously utilized to minimize or prevent such damage. The specific methods of application, as well as the selection and concentration of these compounds will, of course, vary depending upon such circumstances as geographic area, climate, topography, plant tolerance, etc. For specific circumstances, one skilled in the art may readily determine the proper compound, concentration, and method of application by routine experimentation. The compounds are particularly useful as insecticides, nematicides and acaricides, for foliar and/or soil application.

The advantages and the important features of the present invention will be more apparent from the following examples.

EXAMPLES

Example 1

Preparation of 3-Nitro-4-Hydroxybiphenyl

In a one liter reactor equipped with a condenser, a dropping funnel, and a thermometer was charged 68 grams of 4-hydroxybiphenyl and 300 mL of methyl t-butyl ether (MTBE) until all the biphenyl dissolved in the solution at 20° C.

66.6 Grams of 70% nitric acid was intoduced into the dropping funnel and then added dropwise to the one liter reactor over a half hour period while maintaining the temperature below 40° C. The solution turned yellow.

After the addition was complete, the reaction was permitted to run for two hours at room temperature. Two hundred mL of the solvent was then evaporated and the product was washed with water, filtered, and dried. A 98% yield was obtained with a 98–99% assay.

Example 2

Preparation of 4-Methoxy-3-Biphenylhydrazine Hydrochloride (1) Diazonium Salt Preparation Into a vessel equipped with a thermometer, a condenser, and a cooling system and containing 450 mL of water and 45 mL of HCl (concentrated 36.5%) was added 84.7 grams (0.36 mol) of 3-amino-4-methoxy biphenyl hydrochloride (AMBPH). The AMBPH solution was cooled to −5° C. A 30% (27.6 grams, 0.39 mol) sodium nitrite solution was prepared and transferred dropwise via a dropping funnel to the AMBPH solution to keep the temperature below 0° C. After the addition was complete, the reaction was continued for one hour.

(2) Potassium Sulfite Solution Preparation 80.8 Grams of potassium hydroxide was dissolved in 400 mL of water and placed in a two liter reactor. Sulfur dioxide gas was bubbled into the reactor until the pH of the solution was 7.5, whereupon the solution was cooled to 0° C.

(3) Diazo Sulfonate Solution Preparation

The diazonium salt solution was added to the potassium sulfite solution at 0° C. The color of the solution immediately turned a dark orange. The solution was stirred for half an hour at 0° C. and then heated to 50° C. The color of the solution turned yellow during the heating. The mixture was then stirred at 50° C. for another half-hour. The pH was between 5.8 and 6.

(4) Reduction

46 Grams of potassium hydroxide was dissolved in 50 mL of water and the solution was transferred to the diazo sulfonate solution, causing the pH to increase to 12–13. A quantity of 110.4 grams of sodium dithionite ($Na_2S_2O_4$) was added to reduce the diazo sulfonate. A pale yellow solution formed. The reaction was maintained at 50° C. for one hour.

(5) Hydrolysis to 4-Methoxy-3-Biphenylhydrazine Hydrochloride

Hydrogen chloride gas was bubbled into the reactor to hydrolyze the diazinesulfonate to the hydrazine hydrochloride. The addition was continued until the pH was 0.5. After the addition was complete, the temperature was raised to 75° C. for two hours. This was followed by cooling to 25° C. The agitation was stopped and the reaction mixture was permitted to set overnight. 4-Methoxy-3-biphenylhydrazine hydrochloride precipitated out and was isolated by filtration. A yield of 90–95% was obtained.

In view of the many changes and modifications that can be made without departing from principles underlying the invention, reference should be made to the appended claims for an understanding of the scope of the protection to be afforded the invention.

What is claimed is:

1. A method for making a compound of the structural formula

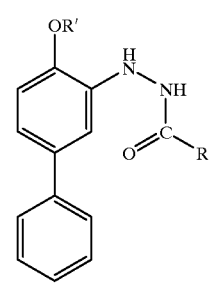

I wherein R is selected from the group consisting of H, $C_1$–$C_6$ alkyl, $C_1$–$C_6$ alkoxy, $C_3$–$C_6$ cycloalkoxy, haloalkyl, alkoxyalkyl, arylalkoxy, alkenyl, alkylthio, alkoxycarbonyl, alkylamino, heteroaryl, arylalkyl, haloalkoxy, aryloxy, and $C_3$–$C_6$ cycloalkyl and R' is $C_1$–$C_6$ alkyl, the wherein the method comprises the steps of:

A) selecting as a starting material a compound of the structural formula

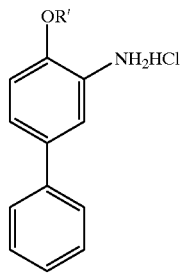

III

B) reacting compound III with sodium nitrite in the presence of HCl to form the diazonium salt IV

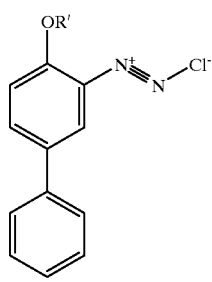

IV

C) adding compound IV to freshly prepared alkali metal sulfite prepared by purging sulfur dioxide into an alkali metal hydroxide until the pH is between 7.3 and 7.5, thereby forming compound V

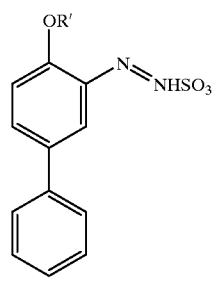

V

D) reducing compound V with an alkali metal dithionite to form compound VI

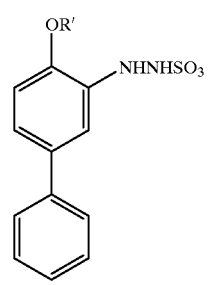

VI

E) hydrolyzing compound VI under acid conditions to form compound VII

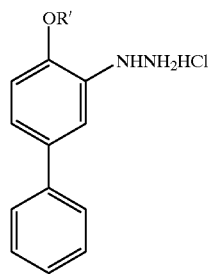

VII and

F) acylating compound VII to form compound I.

2. The method of claim 1 wherein R is $C_1$–$C_6$ alkoxy.

3. The method of claim 2 wherein R is isopropoxy.

4. The method claim 1 wherein the alkali metal hydroxide is sodium hydroxide and the alkali metal sulfite is sodium sulfite.

5. The method claim 1 wherein the alkali metal hydroxide is potassium hydroxide and the alkali metal sulfite is potassium sulfite.

6. The method of claim 1 wherein the alkali metal dithionite is sodium dithionite.

7. A method for making compounds having the structural formula I:

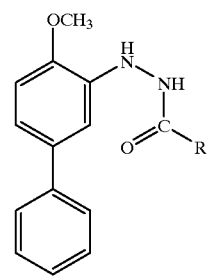

I wherein R is $C_1$–$C_6$ alkoxy, comprising the steps of:

A) selecting as a starting material a compound of the structural formula

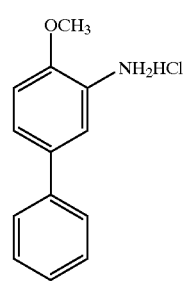

III

B) reacting compound III with sodium nitrite in the presence of HCl to form the diazonium salt IV

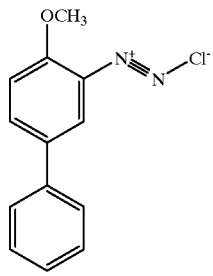
IV

C) adding compound IV to freshly prepared alkali metal sulfite prepared by purging sulfur dioxide into an alkali metal hydroxide until the pH is between 7.3 and 7.5, thereby forming compound V

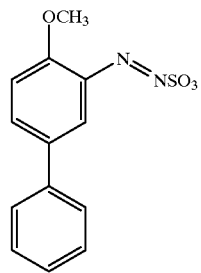
V

D) reducing compound V with an alkali metal dithionite to form compound VI

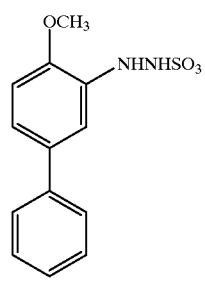
VI

E) hydrolyzing compound VI under acid conditions to form compound VII

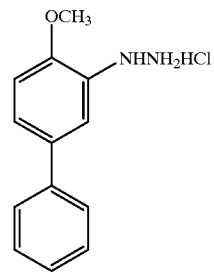
VII and

F) acylating compound VII to form compound I.

8. The method of claim 7 wherein R is isopropoxy.

* * * * *